US00PP08430P

United States Patent [19]

Kientzler

[11] Patent Number: Plant 8,430

[45] Date of Patent: Oct. 19, 1993

[54] IMPATIENS PLANT NAMED OCTAVIA

[75] Inventor: Ludwig Kientzler, Gensingen, Fed. Rep. of Germany

[73] Assignee: Paul Ecke Ranch, Inc., Encinitas, Calif.

[21] Appl. No.: 921,835

[22] Filed: Jul. 30, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new and distinct cultivar of Impatiens plant named Octavia, characterized by its large, violet and red bicolor flowers which are somewhat cupped, compact growth with excellent self-branching, dark bronze-green foliage with red midveins, floriferous habit, and by its suitability to pot or hanging basket culture.

1 Drawing Sheet

The present invention relates to a new and distinct cultivar of plant known as Impatiens and commercially known as New Guinea Impatiens. The new cultivar is known by the cultivar name Octavia, and was developed by the inventor Ludwig Kientzler in Gensingen, Federal Republic of Germany by crossing the cultivar designated C-280 (seed parent) with the cultivar Celerio (pollen parent). Celerio is disclosed in U.S. Plant Pat. No. 7,584.

Asexual reproduction by terminal (stem tip) cuttings taken by me or under my supervision at Gensingen, Federal Republic of Germany, has shown that the unique features of this new Impatiens are stabilized and are reproduced true to type in successive propagations.

The following characeristics distinguish the new Impatiens from both its parent varieties and other cultivars of this general type known and used in the floriculture industry:

1. Robust growth and excellent self-branching characteristics. Plants in 16.5 cm pots were 24 cm tall and 40 cm wide, ten weeks after planting.
2. Large, violet and red bicolor flowers. Flower petals do not lie in a flat plane and are somewhat cupped, giving depth to the flower presentation. Open flowers measure 6 cm or greater in diameter.
3. Very floriferous. Plants in 16.5 cm pots are in flower 8 weeks after planting.
4. Dark bronze-green, glossy foliage with bright red midveins provides a pleasing contrast to the bright flower color.
5. Octavia is well suited for 4" and 6" pot culture, and makes excellent hanging baskets.

Octavia is similar in many respects to the parent cultivar Celerio, differing from Celerio in the following respects. Octavia has larger flowers than Celerio. Octavia normally produces one flower per leaf, whereas Celerio generally has two flowers per leaf. The flower colors are distinctly different. Octavia is a purple violet (80C), compared to the red-purple (72C) flower color of Celerio.

The accompanying colored photograph is a top perspective view of the new cultivar, showing color as true as it is reasonably possible to obtain in a colored reproduction of this type.

The following is a detailed description of my new Impatiens cultivar based on plants grown under commercial practice in Encinitas, Calif. Plants were started as rooted cuttings and were transplanted in mid-February into 16.5 cm (6.5 inch) pots, one pot per plant. By early May, plants were growing vigorously and were in flower. The values, measurements and observations noted below were taken from plants in full bloom in early May.

Color references are made to The Royal Horticultural Society Colour Chart (R.H.S.), except where general terms of ordinary dictionary significance are used.

Parentage: Cross between C-280 (seed) and Celerio (pollen).

Asexual reproduction:

A. *Cutting type.*—Tip, with stems 2–3 cm long developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance.

B. *Habit of growth.*—Vigorous, self-branching habit, producing whorls of leaves and flowers. Growth is indeterminate and flowering is continuous.

C. *Foliage description.*—Leaves are simple. Lower leaves on stems are opposite. Higher leaves in whorls of 3–5, but predominately 5. 1. Leaf shape: Ovate to elliptic. Leaf blade tipes are acuminate; bases are acute. 2. Leaf blade size: Mature leaves 10–11 cm long and 4 to 4.5 cm wide. 3. Petiole length: Approximately 2.5 cm. 4. Leaf margin: Ciliated. 5. Leaf texture: Slightly rugose. a. Upper surface: Glabrous. b. Under surface: Glabrous. 6. Leaf color: Dark bronze-green with a red midvein. a. Upper surface: Near 147A. b. Under surface: Greyed purple near 183A-B. 7. Venation: Pinnate.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus 2 rudimentary sepals fused into the under surface of the superior petal. A spur originates from the base of the inferior sepal. Spur is violet with a green tip and approximately 4.5 cm long.

D. *Flowers borne.*—Singly, on reddish-green pedicels about 4.5 cm long.

E. *Quantity of flowers.*—One flower per leaf. Flowers occur progressively around the whorl of leaves so that tight buds to mature flowers are visible at the same time.

F. *Petals.*—Petals open less than perpendicular to the pedicel so the plane of the flower surface is slightly cupped. 1. Number of petals: Five (5) petals, all overlapping. 2. Shape: All petals are heart-shaped. Superior petal has a broad base. Other petals have a pointed base. 3. Color: Violet and red bicolored petals. a. Upper surface: Periphery near 80C, midvein and base near 64B. b. Under surface: Periphery near 72C, midvein and base 61C. 4. Flower size: Up to 6 cm or larger in diameter.

G. *Reproductive organs.*—Flowers are monoecious. 1. Stamens: Five (5), broad and fused to form a tube around the ovary. 2. Anther: Hooded and cream colored. 3. Pollen: Cream colored. 4. Stigma: Five pointed star, colorless. 5. Styles: Very short. 6. Ovary: 5-celled, 4–5 mm long until fertilized. Grows to 1 cm or longer after fertilization; purple.

Resistance to disease: Good resistance to common stem and root disease, Rizoctonia and Pythium. Botrysis may be a problem in humid or mist propagation environments, but no greater than with other New Guinea Impatiens cultivars.

I claim:

1. A new and distinct cultivar of Impatiens plant named Octavia, as illustrated and described.

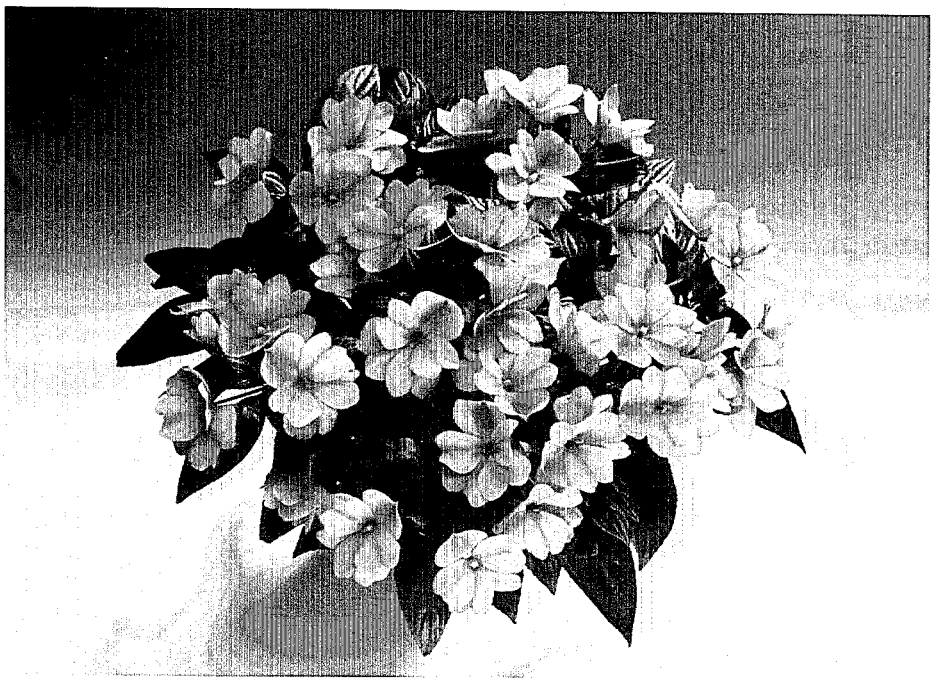

* * * * *